US006855504B2

(12) United States Patent
Fogarty

(10) Patent No.: US 6,855,504 B2
(45) Date of Patent: Feb. 15, 2005

(54) IN VIVO HIGH THROUGHPUT TOXICOLOGY SCREENING METHOD

(75) Inventor: Patrick Fogarty, San Mateo, CA (US)

(73) Assignee: TOSK, Inc., Santa Cruz, CA (US)

( * ) Notice: Subject to any disclaimer, the term of this patent is extended or adjusted under 35 U.S.C. 154(b) by 86 days.

(21) Appl. No.: 10/024,464

(22) Filed: Dec. 19, 2001

(65) Prior Publication Data

US 2002/0176821 A1 Nov. 28, 2002

Related U.S. Application Data

(63) Continuation of application No. 09/472,654, filed on Dec. 27, 1999, now Pat. No. 6,365,129.
(60) Provisional application No. 60/147,220, filed on Aug. 4, 1999.

(51) Int. Cl.$^7$ .............................................. G01N 33/53
(52) U.S. Cl. .......................... 435/7.1; 424/9.1; 424/9.2; 435/7.21; 435/7.22; 435/7.31; 435/7.32; 435/4; 435/29; 436/501; 436/815
(58) Field of Search ..................... 424/9.1, 9.2; 435/29, 435/7.1, 7.21, 7.22, 7.31, 7.32, 4; 436/501, 815

(56) References Cited

U.S. PATENT DOCUMENTS

| | | | |
|---|---|---|---|
| 4,444,891 A | * | 4/1984 | Miwa et al. .................... 436/2 |
| 5,094,944 A | | 3/1992 | Hayes |
| 5,180,838 A | | 1/1993 | Morand et al. |
| 5,225,333 A | | 7/1993 | Krause et al. |
| 5,441,934 A | | 8/1995 | Krapcho et al. |
| 5,506,099 A | | 4/1996 | Carozzi et al. |
| 5,593,862 A | | 1/1997 | Hall et al. |
| 5,665,555 A | | 9/1997 | Sweeney et al. |
| 5,711,932 A | * | 1/1998 | Hirsh et al. .................... 424/9.1 |
| 5,753,434 A | | 5/1998 | Ryner et al. |
| 5,760,181 A | | 6/1998 | De Greve et al. |
| 5,780,246 A | | 7/1998 | Sanders et al. |
| 5,827,679 A | | 10/1998 | Moore et al. |
| 6,008,046 A | | 12/1999 | Ffrench-Constant et al. |
| 6,051,760 A | | 4/2000 | Koziel et al. |
| 6,063,756 A | | 5/2000 | Donovan et al. |
| 6,365,129 B1 | * | 4/2002 | Fogarty ....................... 424/9.2 |

FOREIGN PATENT DOCUMENTS

| | | | |
|---|---|---|---|
| JP | 11142392 A | 5/1999 | |
| WO | WO99/16310 | 4/1999 | |
| WO | WO99/37672 | 7/1999 | |
| WO | WO-99/37672 A1 | * 7/1999 | ........... C07K/14/00 |
| WO | WO99/55906 | 11/1999 | |
| WO | WO99/58652 | 11/1999 | |
| WO | WO99/64586 | 12/1999 | |

OTHER PUBLICATIONS

Lynch et al. (1991). Evaluation of Drosophila for screening developmental toxicants: test results with eithteen chemicals and presentation of a new Drosophila bioassay. Teratogenesis Carcinogen. Mutagen. 11:147–173.*

Wasserkort et al. (1997). Screening toxic effects of volatile organic compounds using Drosophila melanogaster. J. Appl. Toxicol. 17(2):119–125.*

Wells (1998). High–throughput worms. Chem. Biol. 5(6):R147–R148.*

Goss, et al., "Utilization of Alternative Species for Toxicity Testing: an Overview," J. of Applied Toxicology, V. 5 (4), 1985, pp. 193–219.

Lynch, et al., "Evaluation of Drosophila for Screening Developmental Toxicants . . . ," Teratogenesis, Carcinogenesis, and Mutagenesis 11, 1991, pp. 147–173.

Haber, et al., "Development of a Mechanism of Action–Based Screen for Anthelmintic Microbial Metabolites with Avermectinlike Activity and Isolation of Milbemycin–Producing Streptomyces Strains," Antimicrobial Agents and Chemotherapy, Sep. 1991, V. 35(9), pp. 1811–1817.

Wells, "High Throughput Worms," Chemistry and Biology, Jun. 1998, pp. R147–R148.

Farkas, et al. Toxicit5y Test of Antimicrobial Active Compounds, Their Derivatives and Metabolites, on Cell Cultures. Drugs, Biochem., Metab., Sci. Mater. Pap. Colloq. (Editied by Klebovich, et al.) Budapest, hung.: Hung. Chem. Soc., Biochem. Sect., 1981, pp. 277–280.

Kolarova, et al. Poliziti Testu Na Rrybich Bunecnych Kulturach Ve Vodni Toxikologii. Vodni. Hospod. 1997, vol. 47, No. 10, pp. 327–329. (Especially Abstract).

Petitmermet, et al. Toxicity Screening of Waste Products Using Cell Culture Techniques. Monit. Verif. Biorem., Pap. 1995, pp. 223–232.

Smith, et al. Chick Embryo Limb Bud Cell Culture For Screening Environmental Contaminants. Environmental Toxicology and Risk Assessment: Modeling and Risk Assessment, vol. 6, 1997, No. 1317, pp. 402–411.

Taylor, et al. Evaluation of a Chronic Toxicity Test Using Growth of the Insect *Chironomus riparius Meigen*. Bioindic. Environ. Manage., 1991, pp. 343–352.

* cited by examiner

Primary Examiner—Christopher L. Chin
(74) Attorney, Agent, or Firm—Bret E. Field; Bozicevic, Field & Francis

(57) ABSTRACT

A high throughput toxicology screening method is provided. In the subject method, at least 10 different compound compositions are tested simultaneously. Each compound composition is tested by contacting it with a plurality, e.g. from about 10 to 1000, of non-mammalian multi-cellular organisms and determining the effect of the compound composition on the organisms. The multi-cellular organisms employed in the subject methods are small, have differentiated tissues and organs and have a rapid generation time. The subject high throughput screening methods find use in a variety of applications, and are particularly suited for use in the toxicology screening of libraries of compounds, such as libraries of combinatorially produced compounds.

16 Claims, No Drawings

IN VIVO HIGH THROUGHPUT TOXICOLOGY SCREENING METHOD

CROSS REFERENCE TO RELATED APPLICATIONS

Pursuant to 35 U.S.C § 119 (e), this application is continuation of U.S. patent application Ser. No. 09/472,654, filed Dec. 27, 1999 and now issued a U.S. Pat. No. 6,365, 129; which application claims priority to the filing date of the U.S. patent application Ser. No. 60/147,220 filed Aug. 4, 1999, the disclosure of which is herein incorporated by reference.

INTRODUCTION

1. Field of the Invention

The field of this invention is toxicology testing, particularly toxicology testing in pharmaceutical research and development.

2. Background of the Invention

During the drug development process, potential therapeutic agents or drug candidates must be demonstrated to be both safe and effective for their intended use prior to obtaining FDA approval and subsequent commercialization, at least in the United States. In drug development processes, potential drug candidates are subjected to mutagenicity and toxicology assessments in an effort to demonstrate safety. Mutagenicity analyses take place in bacteria (Ames test), Drosophila (Mueller-5 test), and in mammalian cell culture. However, toxicology analyses are limited to mammalian cell culture and animal model studies. This scheme requires significant time and money to be invested to analyze the toxicity of a candidate drug. As such, toxicology studies are typically performed after successful efficacy assessment for drug candidates.

With the advent of high throughput drug discovery, there is great interest in the pharmaceutical and related industries to streamline the toxicology testing segment of the drug development process. As the number of drug candidates has exploded from 10's per year to 1,000's per year, the toxicology assessment programs have become a severe bottleneck in the drug development process.

Accordingly, there is great interest in the development of new high throughput screening assays which are capable of rapidly providing toxicity data for a large number of different compounds. Of particular interest would be the development of an in vivo high throughput toxicity screening assay.

Relevant Literature

High throughput toxicity screening assays are discussed in: Kelly, "Advances in HTS Toxicology," Genetic Engineering News, Mar. 1, 1999, pg. 14; and Sansome, Drug Discovery Today (1999) 4: 199–201.

SUMMARY OF THE INVENTION

High throughput toxicology screening assays are provided. In the subject methods a plurality of different compound compositions, usually at least 10 different compound compositions, are simultaneously assayed for their toxic activity, if any. Each compound composition in the plurality is assayed for toxicity by contacting it with a population of multi-cellular organisms and determining the effect of the compound composition on the multi-cellular organisms. Multi-cellular organisms that find use in the subject high throughput screening (HTS) assays are those that are small, have differentiated tissues and organs, have a rapid generation time, and are prolific. The subject HTS methods find use in a variety of applications, and are particularly suited for use in the toxicological screening of large numbers of compounds, such as combinatorially produced libraries of compounds.

DESCRIPTION OF THE SPECIFIC EMBODIMENTS

A high throughput toxicology screening method is provided. In the subject method, at least 10 different compound compositions are tested simultaneously. Each compound composition is tested by contacting it with a plurality, e.g. from about 10 to 1000, non-mammalian multi-cellular organisms and determining the effect of the compound composition on the organisms. The multi-cellular organisms employed in the subject methods are small, have differentiated tissues and organs, have a rapid generation time, and are prolific. The subject high throughput screening methods find use in a variety of applications, and are particularly suited for use in the toxicology screening of libraries of compounds, such as libraries of combinatorially produced compounds.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms •a, • •an, "and •the" include plural reference unless the context clearly dictates otherwise. Unless defined otherwise, all technical and scientific terms used herein have the same meaning as commonly understood to one of ordinary skill in the art to which this invention belongs.

As summarized above, the subject invention provides a high throughput screening (HTS) method for simultaneously testing the toxicology of a plurality of different compound compositions. The subject HTS assays are in vivo toxicology assays, by which is meant that they determine the effect of a compound on a living, multi-cellular organism. As such, the subject HTS assays are distinguished from in vitro assays, in which cell cultures are employed.

In the subject HTS assays, a plurality of different compounds are simultaneously tested. More specifically, a plurality of different compound compositions are simultaneously tested. Different compound compositions differ from each other in at least one of the following characteristics: (a) they are made up of compounds that differ by molecular formula; or (b) they are made up of compounds of the same molecular formula but the compounds are present in different concentrations. In other words, any two given compound compositions are different if they are either made up of compounds that differ by molecular formula or are made up of the same type of compound but differ with respect to concentration of that compound. For example, a plurality of different compound compositions may include 4 different types of compounds that differ by molecular formula, where each specific type of compound is present in three different concentrations, such that the plurality is made up of 12 different compound compositions.

By simultaneously tested is meant that each of the compound compositions in the plurality are tested at substantially the same time. Thus, all of the compound compositions in the plurality are assayed for their toxicological effects in parallel. The number of compound compositions in the plurality of compound compositions that are simultaneously tested is typically at least about 10, where in certain embodiments the number may be at least about 100 or at least about 1000, where the number of compound compositions tested may be higher. In general, the number of compound compositions that are tested simultaneously in the subject HTS methods ranges from about 10 to 10,000, usually from about 100 to 10,000 and in many embodiments from about 1000 to 5000.

In the subject methods, each individual compound composition in the plurality is individually assayed for toxicology. Each compound composition is individually assayed for its toxicity by contacting the compound composition with a plurality of non-mammalian multi-cellular organisms and determining the effect of the compound composition (or lack thereof) on the organisms of the plurality. As the organisms employed in the subject methods are multi-cellular, they include differentiated tissues and organs. They are further characterized by being relatively small, where by small is meant at least about 0.001 g, usually at least about 0.01 g and more usually at least about 0.1 g, where the average mass of each organism in the plurality may be as great as 10 g or greater, but typically does not exceed about 100 g and usually does not exceed about 1,000 g. The multi-cellular organisms employed in the subject HTS methods are also characterized by having a rapid generation time. A rapid generation time is important to maintain the breeding colony plus supply enough organisms that will be prolific enough to produce on average at least about 100 progeny per day, which is the minimum requirement for high throughput sceening. For *Drosophila,* this minimum population of flies can range from 10 to 300, usually from 50 to 150.

A number of different types of non-mammalian multi-cellular organisms may be employed in the subject methods, where these types of organisms include insects, amphibians, fish, and the like. Specific organisms of interest include: *Xenopus,* Zebrafish, *Caenerhabditis, Drosophila* and the like. Of particular interest in many embodiments are invertebrate animals, particularly members of the phylum arthropoda, and more particularly members of the class insecta. Of particular interest in many embodiments are flies. In many preferred embodiments, the flies are members of the family Drosophilidae, where the animal is often a *Drosophila melanogaster.* The multi-cellular organisms employed in the subject invention may be at any stage of their life, e.g. in the larval stage, in the adult stage, etc.

One specific multi-cellular organism of interest is a non-mammalian transgenic animal having an adult onset neurodegenerative phenotype, e.g. a transgenic *Drosophila melanogaster* having an adult onset neurodegenerative phenotype, as described in U.S. Patent Application Ser. No. 60/125,586, the disclosure of which is herein incorporated by reference. Another multi-cellular organism of particular interest is the non-mammalian transgenic animal for cellular proliferative diseases, e.g. a transgenic *Drosophila melanogaster* having a neoplastic phenotype, as described in U.S. Patent Application Ser. No. 60/147,433 filed Aug. 4, 1999, the disclosure of which is herein incorporated by reference. Also of interest are non-transgenic non-mammalian animals.

In the subject assay methods, each compound composition is brought into contact with the population of multi-cellular organisms in a manner such that the active agent of the compound composition is capable of exerting activity on at least a substantial portion of, if not all of, the individual organisms of the population. By substantial portion is meant at least 40 number %, usually at least 50 number % and more usually at least 60 number %, where the number % may be substantially higher and in many embodiments can be as high as 80, 90 or 95 number % or higher. Generally, each compound agent is contacted with the members of the population in a manner such that the active agent of the composition is internalized by the organisms. Typically internalization will be by ingestion, i.e. orally, such that that each compound composition will generally be contacted with the plurality of organisms by incorporating the compound composition in the nutrient medium, e.g. water, aqueous solution of additional nutrient agents, etc., of the organisms. For example, where the multi-cellular organism is a fly, the candidate agent is generally orally administered to the fly by mixing the agent into the fly nutrient medium and placing the medium in the presence of the fly, (either the larva or adult fly, usually the larva) such that the fly feeds on the medium.

As such, the compound composition may be contacted with the population of multi-cellular organisms at any convenient stage during the life cycle of the organism. Thus, depending on the particular organisms employed, the compound composition is contacted with the organisms during an immature life cycle stage, e.g. larval stage, during an adult stage, and the like.

A large number of different types of compounds may be assayed according to the subject invention. Compounds that may be assayed according to the subject HTS methods encompass numerous chemical classes, though typically they are organic molecules, preferably small organic compounds having a molecular weight of more than 50 and less than about 2,500 daltons. Compounds generally comprise functional groups necessary for structural interaction with proteins, particularly hydrogen bonding, and typically include at least an amine, carbonyl, hydroxyl or carboxyl group, preferably at least two of the functional chemical groups. The compounds often comprise cyclical carbon or heterocyclic structures and/or aromatic or polyaromatic structures substituted with one or more of the above functional groups. Compounds of interest are also found among biomolecules including, but not limited to: peptides, saccharides, fatty acids, steroids, purines, pyrimidines, derivatives, structural analogs or combinations thereof.

Compounds of interest are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Screening may be directed to known pharmacologically active compounds and chemical analogs thereof, or to new agents with unknown properties such as those created through rational drug design.

Following contact of the compound composition with the population, the effect of the compound on the members of the population is determined. The effect of the compound on the members of the population is generally determined by evaluating one or more of a number of different phenotypic parameters. Phenotypic parameters that are evaluated in a given HTS assay of the subject invention may vary widely depending, at least in part, on the nature of the multi-cellular organisms being employed. Typically, phenotypic parameters that are evaluated in any given assay include one or more of the following: (1) viability; (2) morphological defects; and (3) fecundity. Specific parameters that may be evaluated include one or more of: (1) lethal dose, e.g. $LD_{50}$, $LD_{10}$ etc.); (2) growth defects; (3) sterility effect dose; (4) developmental defects; (5) neurologic impairment; (5) lifespan modulation, e.g. life span enhancing or shortening; and the like.

In addition to the above parameters that can be evaluated in the subject methods, the gene expression levels of the test organisms can be assayed, e.g. gene expression levels in treated larva, pupa, and/or flies can be evaulated. The genes can be from "houskeeping" genes that provide basic metabolic information to developmental and tissue specific genes to gauge which tissue or cell type is affected and when. A variety of different gene expression protocols, including arrays based protocols, are known to those of skill in the art, including those described in: EP 0 328 829 B1 and U.S. Pat. Nos. 5,468,613; 5,580,726; 5,599,672; 5,512,462; 5,162,209 and 5,162,209, the disclosures of which are herein incorporated by reference. Methods of analyzing differential gene expression are also described in Maniatis, et al., Molecular Cloning, A Laboratory Manual, (Cold Spring Harbor Press, Cold Spring Harbor, N.Y.)(1989); Nucleic Acid Hybridization, A Practical Approach (Hames, B. D., and Higgins, S. J. eds, IRL Press, Oxford)(1985); WO 95/21944; Chalifour, et al., Anal. Biochem. (1994) 216: 299–304; Nguyen et al., Genomics (1995) 29: 207–216; Pietu et al., Genome Res. (1996) 6: 492–503; and Zhao et al., Gene (1995) 166: 207–213.

The effect of the compound on the particular physical parameter or parameters being evaluated may be determined manually or robotically, such that in many embodiments determination of the effect of the compound on the organism is accomplished via an automated procedure.

The effect of the compound on the phenotypic parameter or parameters is then related to the toxicity of the compound. As such, the effect on the phenotypic parameter(s) is employed to derive a toxicity profile for the assayed compound, where toxicity profile refers to the toxic activity of a given compound, i.e. its collection of one or more toxic activities, such as lethality, sterility causing activity, etc.

Because the subject methods are HTS methods in which a plurality of compounds are assayed for toxicity at the same time, any given HTS screen according to the subject invention rapidly provides toxicity profiles for a plurality of compounds. The number of compounds for which toxicity profiles are rapidly provided in any given HTS assay according to the subject invention ranges from about 20 to 50,000, usually from about 50 to 10,000 and more usually from about 500 to 5,000. As the toxicity profiles are rapidly determined, they are determined in generally less than about 14 days, usually less than about 10 days. In many embodiments, they may be determined in less than about 7 days or in a shorter period of time.

In sum, the subject invention as described above provides a high throughput method for toxicity screening of a large number of compounds and/or different concentrations thereof. The subject HTS toxicity screens find use in a variety of different applications in which it is desired to obtain toxicity data for a large number of compounds in a short period of time. Of particular interest in many embodiments is the use of the subject methods to provide in vivo toxicity profiles for individual compound members of libraries or collections of compounds, including combinatorially produced libraries of compounds. As such, the subject HTS toxicology screening assays find use in a number of applications, including drug discovery and development applications.

The subject HTS methods may be part of a multi-step screening process of evaluating candidate therapeutic agents for their efficacy (and safety) in the treatment of disease conditions. In multi-step screening processes of the subject invention, a library of compounds is subjected to screening in a second in vivo model, e.g. a mouse model, following screening via the subject HTS assays. Following the initial screening of the library using the HTS methods of the subject invention, the positive compounds identified by the screen (i.e. those compounds that do not have unacceptable toxicity profiles) are then screened in non-human mammalian animal models, including transgenic non-human mammalian animal models, where the mammalian animal models are generally correlated to the particular target disease condition. In addition, a pre in vivo screening step may be employed, in which the library of compounds is first subjected to an in vitro screening assay for its potential as a therapeutic agent in the treatment of a particular disease condition. Any convenient in vitro screening assay may be employed, where a variety of suitable in vitro screening assays are known to those of skill in the art, e.g. HTS cell culture assays.

The subject HTS toxicity screening assays also find use in the generation of databases of information that include toxicity profiles of a plurality of distinct compounds. As such, the subject invention can be employed to produce a database of toxicity profiles for a variety of compounds. Such a toxicity profile database will typically comprise toxicity profile information as described above, for a number of related compounds. The compounds of interest in a database may be selected and arranged according to various criteria: the types of molecules that are tested, e.g. steroids, antibiotics, antineoplastic agents, etc.; by the source of compounds, e.g. environmental toxins, biologically active extracts from a particular animal or cell, synthetic or natural library of compounds etc.; and the like.

The toxicity profiles and databases thereof may be provided in a variety of media to facilitate their use. "Media" refers to a manufacture that contains the toxicity profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. One format for an output means ranks toxicity profiles possessing varying degrees of similarity to a reference toxicity profile. Such presentation provides a skilled artisan with a ranking of similarities and identifies the degree of similarity contained in the test toxicity profile.

The subject toxicity profile databases find use in a number of different applications. For example, where one has a compound of interest, one can search the database to determine whether that compound is present in the database and, if so, readily identify the toxicity profile of the compound. Alternatively, where one has a novel compound whose profile is not present in the database, but one knows the structure of the compound, one can search the database for similar compounds of similar structure and obtain information regarding the toxicity of the compound of interest through extrapolation. One can also compare a novel toxicity profile of the a compound not present in the database with profiles present in the database in order to identify compounds of similar toxicity to the compound of interest.

The comparison of a toxicity profile obtained from a test compound and toxicity profiles present in the database, i.e. reference toxicity profiles, is accomplished by any suitable deduction protocol, AI system, statistical comparison, etc. Methods of searching databases are known in the art. See, for example, U.S. Pat. No. 5,060,143, which discloses a highly efficient string search algorithm and circuit, utilizing candidate data parallel, target data serial comparisons with an early mismatch detection mechanism. For other examples, see U.S. Pat. Nos. 5,720,009 and 5,752,019, the disclosure of which are herein incorporated by reference.

Also provided by the subject invention are methods of screening libraries of compounds for their antitoxic effect, i.e. hight throughput methods for the identification of antitoxin compounds. In such methods, a library of candidate antitoxin compounds is screened for activity according to the methods described above, where the test population of animals, e.g. flies, will have been previously contacted with the toxin for which an antitoxin is sought or will be concomittantly contacted with the toxin. Toxins of particular interest in many embodiments are those that are toxic in both humans and the test animal, e.g. flies. The animal population is contacted with the toxin of interest using any convenient method, e.g. inclusion of the toxin in the nutrient medium, where the dose of toxin contacted with the population is a lethal dose, e.g. $LD_{95}$. Following contact of the test library of candidate antitoxins with the animal population, those animals that survive are indicative of the animals that were given test compounds that have internalized an agent with the desired anti-toxin activity. Thus, also provided by the subject invention is a high throughput method of screening for compounds having antitoxin activity.

The following examples are offered by way of illustration and not by way of limitation.

EXPERIMENTAL

I. Validation of the Fly Model for Toxicology

In order to determine the extent that the fly model is valid for toxicology assessment studies, an assessment of chemicals with known toxicological profiles and targets is generated using the fly. The chemicals chosen have no substantial toxicity levels (e.g., food dye, sugar, etc.) to ones that are very toxic. The very toxic ones can be broken down into three classes, ones that are generally toxic, ones that are toxic to a cell, tissue, or organ type that is known to be in common with humans and flies, and ones that are toxic to a cell, tissue, or organ type that is specific to humans.

A. Toxicity Tests

The chemical is dissolved in water at or near its saturation point. Serial dilutions of this stock solution are used to rehydrate instant fly media (Fisher Scientific). Specifically, one toxicity assay will comprise of instant fly media rehydrated with pure stock solution of a chemical, while another will be rehydrated with a 10% solution of the chemical (in water). This format will be used to generate data over a 4 to 5 log dose range for each chemical tested.

A known quantity of embryos, typically between 40–50, is used as the input. Specifically, 40 to 50 embryos are counted and placed in the receptacle that contains the media/chemical mixture to be tested. The embryos may be counted manually or by automation (e.g., liquid suspension of embryos flowing through a diode). The larva feed on the media/chemical mixture. All aspects of development from larva stage to adult must proceed normally in the presence of the chemical. The only food and water source available to the larva and flies contains the chemical. It is shown that the variability of and intake amount that can be expected using this protocol by feeding the larva chemicals that are easy to assay. Specifically, Iron, Copper, and zinc have been selected. Sensitive and accurate kits are commercially available to analyze these chemicals down to a concentration of 1 part per million. This will assign quantitative analyses to determine variability between larva in a test receptacle and between larva in different receptacles.

B. Toxicology Assessment

The developing larva and pupa are examined for normal growth and development. Then the adult flies are analyzed for lethality, sterility, developmental defects, and life span alterations. Lethality is determined by dividing the number of adult flies that eclose by the total number of embryos that were placed in the receptacle. Sterility is examined for both males and females by crossing them to normal flies. A physical examination of the adults reveals any visible defects, such as limb defects, tissue formation defects, abnormal coordination, etc. Finally the flies are allowed to live the natural span of their life to determine whether an effect occurred to either shorten or lengthen the average lifespan of the fly.

II. Assays

A. Toxicity Screens

Using standard protocols, including the ones described above for administration to flies, a variety of agents were administered at different doses to mice, rats and flies and the LD for each agent was compared. The results are provided in Table 1.

TABLE 1

Lethal dose toxicity trends are similar between mammals and flies.

| Chemical Tested | Mouse (oral LD50 mg/ml) | Rat (oral LD50 mg/ml) | Fly (oral LD50 mg/ml) |
|---|---|---|---|
| High toxicity | | | |
| sodium azide | 27 | 27 | .05 |
| cadmium chloride | 60 | 88 | .1 |
| clonidine | 135 | 126 | .07 |
| Moderate toxicity | | | |
| metrifonate | 300 | 560 | .04 |
| 4-dimethyl aminopyridine | n/a | 250 | .15 |
| phenylenediamine | 366 | 510 | .2 |
| lithium chloride | 1165 | 526 | .4 |
| Low toxicity | | | |
| disodium phosphate | n/a | 17,000 | 142 |
| niacinamide | 2500 | 3500 | 5 |
| polyvinyl pyrrolidol | 40000 | 100000 | <.4 |
| sodium borate | 2000 | 2660 | 6.5 |
| L-dopa | 2363 | 1780 | .7 |
| bromophenol blue | n/a | n/a | 10 |

The trend for lower to higher toxic agents is similar in flies and mammals. The low toxics were categorized by having an LD50>1,500 mg/kg in mice and rats and these corresponded with a dose of greater than 0.4 mg (the 0.4 mg dose for polyvinyl pyrrolidol was the maximum dose that was administerable to the flies and no toxicity was observed at this level). While the moderate range was defined as having a mouse or rat dose over 150 mg/kg up to 1400 mg/kg. This corresponded with a LD50 dose range of 0.15 to 0.4 for the fly. Finally the high toxic substances in mice and rats had an oral LD50 with less than 150 mg/kg. This corresponded to the fly range that was 0.1 mg dose or less to induce an oral administered LD50. The one outlyer was metrifonate. This chemical is of moderate toxicity in mice and rats, while it is clearly in the high toxic range for flies. As an initial high throughput screen, this pilot study suggests a >90% toxic assessment correspondence with mice and rats. This clearly demonstrates the potential to rapidly and accurately estimate toxicity of unknown compounds.

B. AntiToxicity Screens

The activity of EDTA as an antitoxin was assessed by administering flies toxins in conjunction with EDTA and without EDTA. The results are provided in Table 2.

TABLE 2

EDTA is an effective in vivo anti-toxin in the fruit fly

| Fly food | Yeast Paste | % survival |
|---|---|---|
| 1.1 mM Copper | None | 0 |
| 6.0 mM Zinc | None | 0 |
| No chemical | 25 mM EDTA | 0 |
| 1.1 mM Copper | 25 mM EDTA | 76 |
| 6.0 mM Zinc | 25 mM EDTA | 70 |
| No chemical | None | 84 |
| 0.4 mM Copper | None | 50 |
| 2 mM Zinc | None | 50 |

The chemical EDTA binds to heavy metals, including copper and zinc. This binding can occur in vitro or in vivo. In vivo binding can lead to neutralizing the toxicity of heavy metals to animals. However, since EDTA binds to calcium, it alone has a reasonable amount of toxicity. The above results demonstrate that a known heavy metal antitoxin can be identified using the subject in animal antitoxin system. Shown in Table 2 is the toxic effects of zinc, copper, and EDTA on the fruit fly. The data in Table 2 also show that the flies can survive in the prescence of both heavy metal (e.g., copper or zinc) and EDTA. To ensure that any antitoxin effects from the EDTA would occur in vivo, the heavy metal and EDTA were supplied in two, physically separated food sources. The flies had to eat from the fly food and yeast paste in the proper amount to neutralize the toxic effects, allowing for survival.

It is evident from the above results and discussion that the subject invention provides a valuable new high throughput screening method. As the subject methods employ multicellular organisms, they provide valuable in vivo toxicity data which is often better correlated to activity in humans. Furthermore, the toxic effects on compounds can be determined on a number of different types of cells at substantially the same time. In addition, the subject HTS assays are rapid. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A high throughput toxicology screening method in which at least 10 different compound compositions are simultaneously assayed for toxicity, said method comprising:

simultaneously assaying at least 10 different compound compositions for toxicity, wherein each of said at least 10 different compound compositions is assayed for toxicity by:
   (a) contacting said compound composition with a plurality of non-mammalian multi-cellular organisms; and
   (b) determining the effect of said compound composition on said non-mammalian multi-cellular organisms to estimate the effect of said compound composition on a mammalian organism selected from a rat or a mouse.

2. The screening method according to claim 1, wherein said plurality of non-mammalian multi-cellular organisms ranges from about 10 to 1000.

3. The screening method according to claim 1, wherein said non-mammalian multi-cellular organisms have a rapid generation time.

4. The screening method according to claim 1, wherein said non-mammalian multi-cellular organisms are small.

5. The screening method according to claim 1, wherein said non-mammalian multi-cellular organisms are characterized by the presence of differentiated organs and tissues.

6. A high throughput toxicology screening method in which at least 10 different compound compositions are simultaneously assayed for toxicity, said method comprising:

simultaneously assaying at least 10 different compound compositions for toxicity, wherein each of said at least 10 different compound compositions is assayed or toxicity by:
  (a) contacting said compound composition with a population of from about 10 to 1000 small non-mammalian multi-cellular organisms having a rapid generation time and differentiated organs end tissues; and
  (b) determining the effect of said compound composition on said non-mammalian multi-cellular organisms to estimate the effect of said compound composition on a mammalian organism selected from a rat or a mouse.

7. The method according to claim 6, wherein said population is characterized by producing at least 100 progeny per day.

8. The method according to claim 6, wherein at least 100 compound compositions are tested simultaneously.

9. The method according to claim 6, wherein at least 1000 compound compositions are tested simultaneously.

10. The method according to claim 6, wherein said multi-cellular organism is an insect.

11. The method according to claim 10, wherein said insect is a fly.

12. A high throughput antitoxin screening method in which at least 10 different candidate antitoxin compound compositions are simultaneously assayed for antitoxin activity, said method comprising:
simultaneously assaying at least 10 different candidate antitoxin compound compositions for antitoxin activity, wherein each of said at least 10 different candidate compound compositions is assayed for antitoxin activity by:
  (a) contacting said candidate compound composition with a population of from about 10 to 1000 small non-mammalian multi-cellular organisms having a rapid generation time and differentiated organs and tissues which have been contacted with a toxin; and
  (b) determining the effect of said compound composition on said non-mammalian multi-cellular organisms to estimate the effect of said compound composition on a mammalian organism selected from a rat or a mouse.

13. The method according to claim 12, wherein said population is characterized by producing at least 100 progeny per day.

14. The method according to claim 12, wherein at least 100 candidate compound compositions are tested simultaneously.

15. The method according to claim 6, wherein at least 1000 candidate compound compositions are tested simultaneously.

16. The method according to claim 6, wherein said multi-cellular organism is an insect.

* * * * *